(12) United States Patent
Mickley

(10) Patent No.: US 8,790,388 B2
(45) Date of Patent: Jul. 29, 2014

(54) STENT WITH REDUCED PROFILE

(75) Inventor: Timothy J. Mickley, Corcoran, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 109 days.

(21) Appl. No.: 13/410,543

(22) Filed: Mar. 2, 2012

(65) Prior Publication Data
US 2012/0226342 A1    Sep. 6, 2012

Related U.S. Application Data

(60) Provisional application No. 61/448,918, filed on Mar. 3, 2011.

(51) Int. Cl.
A61F 2/06    (2013.01)

(52) U.S. Cl.
USPC ......................................................... 623/1.11

(58) Field of Classification Search
USPC .............. 606/108; 623/1.11, 1.12, 1.13, 1.14, 623/1.15, 1.16, 1.17, 1.18, 1.19, 1.2, 1.21, 623/1.28
See application file for complete search history.

(56) References Cited

U.S. PATENT DOCUMENTS

| | | | |
|---|---|---|---|
| 2,836,181 A | 5/1958 | Tapp | |
| 3,105,492 A | 10/1963 | Jeckel | |
| 3,272,204 A | 9/1966 | Artandi et al. | |
| 3,490,975 A | 1/1970 | Lightwood et al. | |
| 3,509,883 A | 5/1970 | Dibelius | |
| 3,526,228 A | 9/1970 | Lyng | |
| 3,562,820 A | 2/1971 | Braun | |
| 3,635,215 A | 1/1972 | Shea et al. | |
| 3,657,744 A | 4/1972 | Ersek | |
| 3,771,526 A | 11/1973 | Rudle | |
| 3,868,956 A | 3/1975 | Alfidi et al. | |

(Continued)

FOREIGN PATENT DOCUMENTS

| CA | 2248718 | 9/1997 |
|---|---|---|
| DE | 29702671 | 4/1997 |

(Continued)

OTHER PUBLICATIONS

Beyar et al, "The BeStent; The Parallel-Serial Jang Stents" , Handbook of Coronary Stents, Second Edition, 158-171 & 229-234 (1998).

(Continued)

*Primary Examiner* — Jonathan W Miles
(74) *Attorney, Agent, or Firm* — Vidas, Arrett & Steinkraus, P.A.

(57) ABSTRACT

Medical devices, systems, and techniques are described for reducing the profile of a stent. In one example, a stent having a reduced state and an expanded state includes a plurality of interconnected annular rings arranged about a longitudinal axis, each of the plurality of annular bands comprising a plurality of peaks and a plurality of troughs, wherein in the reduced state, at least one of the plurality of peaks of at least one of the plurality of rings is positioned a first distance from the longitudinal axis, another one of the plurality of peaks being positioned a second distance from the longitudinal axis, the first distance being less than the second distance, and wherein in the expanded state, the plurality of peaks of the stent being positioned at substantially the same distance from the longitudinal axis.

18 Claims, 11 Drawing Sheets

(56) References Cited

U.S. PATENT DOCUMENTS

| | | | |
|---|---|---|---|
| 3,993,078 A | 11/1976 | Bergentz et al. | |
| 4,078,167 A | 3/1978 | Banas et al. | |
| 4,127,761 A | 11/1978 | Pauley et al. | |
| 4,130,904 A | 12/1978 | Whalen | |
| 4,140,126 A | 2/1979 | Choudhury | |
| 4,141,364 A | 2/1979 | Schultze | |
| 4,164,045 A | 8/1979 | Bokros et al. | |
| 4,214,587 A | 7/1980 | Sakura, Jr. | |
| 4,300,244 A | 11/1981 | Bokros | |
| 4,313,231 A | 2/1982 | Koyamada | |
| 4,319,363 A | 3/1982 | Ketharanathan | |
| 4,425,908 A | 1/1984 | Simon | |
| 4,441,215 A | 4/1984 | Kaster | |
| 4,470,407 A | 9/1984 | Hussein | |
| 4,501,264 A | 2/1985 | Rockey | |
| 4,503,569 A | 3/1985 | Dotter | |
| 4,512,338 A | 4/1985 | Balko et al. | |
| 4,535,770 A | 8/1985 | Lemole | |
| 4,550,447 A | 11/1985 | Seiler, Jr. et al. | |
| 4,553,545 A | 11/1985 | Maass et al. | |
| 4,560,374 A | 12/1985 | Hammerslag | |
| 4,580,568 A | 4/1986 | Gianturco | |
| 4,597,389 A | 7/1986 | Ibrahim et al. | |
| 4,647,416 A | 3/1987 | Seiler, Jr. et al. | |
| 4,649,922 A | 3/1987 | Wiktor | |
| 4,655,771 A | 4/1987 | Wallsten | |
| 4,655,776 A | 4/1987 | Lesinski | |
| 4,665,918 A | 5/1987 | Garza et al. | |
| 4,681,110 A | 7/1987 | Wiktor | |
| 4,693,721 A | 9/1987 | Ducheyne | |
| 4,733,665 A | 3/1988 | Palmaz | |
| 4,739,762 A | 4/1988 | Palmaz | |
| 4,740,207 A | 4/1988 | Kreamer | |
| 4,760,849 A | 8/1988 | Kropf | |
| 4,762,128 A | 8/1988 | Rosenbluth | |
| 4,768,507 A | 9/1988 | Fischell et al. | |
| 4,769,029 A | 9/1988 | Patel | |
| 4,771,773 A | 9/1988 | Kropf | |
| 4,776,337 A | 10/1988 | Palmaz | |
| 4,786,507 A | 11/1988 | Schmidt | |
| 4,787,899 A | 11/1988 | Lazarus | |
| 4,795,458 A | 1/1989 | Regan | |
| 4,795,465 A | 1/1989 | Marten | |
| 4,800,882 A | 1/1989 | Gianturco | |
| 4,820,298 A | 4/1989 | Leveen et al. | |
| 4,830,003 A | 5/1989 | Wolff et al. | |
| 4,842,575 A | 6/1989 | Hoffman, Jr. et al. | |
| 4,848,343 A | 7/1989 | Wallsten et al. | |
| 4,851,009 A | 7/1989 | Pinchuk | |
| 4,856,516 A | 8/1989 | Hillstead | |
| 4,872,874 A | 10/1989 | Taheri | |
| 4,877,030 A | 10/1989 | Beck et al. | |
| 4,878,906 A | 11/1989 | Lindemann et al. | |
| 4,886,062 A | 12/1989 | Wiktor | |
| 4,913,141 A | 4/1990 | Hillstead | |
| 4,922,905 A | 5/1990 | Strecker | |
| 4,950,227 A | 8/1990 | Savin et al. | |
| 4,950,258 A | 8/1990 | Kawai et al. | |
| 4,994,071 A | 2/1991 | MacGregor | |
| 5,015,253 A | 5/1991 | MacGregor | |
| 5,019,090 A | 5/1991 | Pinchuk | |
| 5,035,706 A | 7/1991 | Giantureo et al. | |
| 5,037,392 A | 8/1991 | Hillstead | |
| 5,059,211 A | 10/1991 | Stack et al. | |
| 5,061,275 A | 10/1991 | Wallsten et al. | |
| 5,064,435 A | 11/1991 | Porter | |
| 5,091,205 A | 2/1992 | Fan | |
| 5,091,211 A | 2/1992 | Richard | |
| 5,092,877 A | 3/1992 | Pinchuk | |
| 5,102,417 A | 4/1992 | Palmaz | |
| 5,104,399 A | 4/1992 | Lazarus | |
| 5,104,404 A | 4/1992 | Wolff | |
| 5,108,415 A | 4/1992 | Pinchuk et al. | |
| 5,108,417 A | 4/1992 | Sawyer | |
| 5,122,154 A | 6/1992 | Rhodes | |
| 5,133,732 A | 7/1992 | Wiktor | |
| 5,135,536 A | 8/1992 | Hillstead | |
| 5,139,480 A | 8/1992 | Hickle et al. | |
| 5,147,385 A | 9/1992 | Beck et al. | |
| 5,147,400 A | 9/1992 | Kaplan et al. | |
| 5,158,548 A | 10/1992 | Lau et al. | |
| 5,163,952 A | 11/1992 | Froix | |
| 5,195,984 A | 3/1993 | Schatz | |
| 5,197,978 A | 3/1993 | Hess | |
| 5,217,483 A | 6/1993 | Tower | |
| 5,226,913 A | 7/1993 | Pinchuk | |
| 5,282,823 A | 2/1994 | Schwartz et al. | |
| 5,282,824 A | 2/1994 | Gianturco | |
| 5,292,331 A | 3/1994 | Boneau | |
| 5,304,200 A | 4/1994 | Spaulding | |
| 5,344,425 A | 9/1994 | Sawyer | |
| 5,354,308 A | 10/1994 | Simon et al. | |
| 5,354,309 A | 10/1994 | Schnepp-Pesch et al. | |
| 5,356,423 A | 10/1994 | Tihon et al. | |
| 5,366,504 A | 11/1994 | Andersen et al. | |
| 5,383,892 A | 1/1995 | Cardon et al. | |
| 5,389,106 A | 2/1995 | Tower | |
| 5,405,377 A | 4/1995 | Cragg | |
| 5,411,552 A | 5/1995 | Andersen et al. | |
| 5,443,498 A | 8/1995 | Fontaine | |
| 5,449,373 A | 9/1995 | Pinchasik et al. | |
| 5,522,881 A | 6/1996 | Lentz | |
| 5,591,197 A | 1/1997 | Orth et al. | |
| 5,609,627 A | 3/1997 | Goicoechea et al. | |
| 5,628,782 A | 5/1997 | Myers et al. | |
| 5,630,829 A | 5/1997 | Lauterjung | |
| 5,632,771 A | 5/1997 | Boatman et al. | |
| 5,643,580 A | 7/1997 | Subramaniam | |
| 5,649,952 A | 7/1997 | Lam | |
| 5,697,971 A | 12/1997 | Fischell et al. | |
| 5,707,386 A | 1/1998 | Schnepp-Pesch et al. | |
| 5,716,365 A | 2/1998 | Goicoechea et al. | |
| 5,716,393 A | 2/1998 | Lindenberg et al. | |
| 5,718,713 A | 2/1998 | Frantzen | |
| 5,725,547 A | 3/1998 | Chuter | |
| 5,725,572 A | 3/1998 | Lam et al. | |
| 5,735,893 A | 4/1998 | Lau et al. | |
| 5,741,317 A | 4/1998 | Ostrow | |
| 5,741,327 A | 4/1998 | Frantzen | |
| 5,746,745 A * | 5/1998 | Abele et al. | 623/1.11 |
| 5,755,770 A | 5/1998 | Ravenscroft | |
| 5,755,776 A | 5/1998 | Al-Saadon | |
| 5,755,781 A | 5/1998 | Jayaraman | |
| 5,766,238 A | 6/1998 | Lau et al. | |
| 5,776,161 A | 7/1998 | Globerman | |
| 5,776,183 A | 7/1998 | Kanesaka et al. | |
| 5,800,520 A | 9/1998 | Fogarty et al. | |
| 5,800,521 A | 9/1998 | Orth | |
| 5,807,404 A | 9/1998 | Richter | |
| 5,810,872 A | 9/1998 | Kanesaka et al. | |
| 5,814,063 A | 9/1998 | Freitag | |
| 5,824,046 A | 10/1998 | Smith et al. | |
| 5,824,059 A | 10/1998 | Wijay | |
| 5,827,321 A | 10/1998 | Roubin et al. | |
| 5,836,966 A | 11/1998 | St. Germain | |
| 5,843,168 A | 12/1998 | Dang | |
| 5,855,597 A | 1/1999 | Jayaraman | |
| 5,855,600 A | 1/1999 | Alt | |
| 5,858,556 A | 1/1999 | Eckert et al. | |
| 5,861,027 A | 1/1999 | Trapp | |
| 5,868,780 A | 2/1999 | Lashinski et al. | |
| 5,873,906 A | 2/1999 | Lau et al. | |
| 5,876,432 A | 3/1999 | Lau et al. | |
| 5,879,381 A | 3/1999 | Moriuchi et al. | |
| 5,895,407 A | 4/1999 | Jayaraman | |
| 5,911,754 A | 6/1999 | Kanesaka et al. | |
| 5,913,895 A | 6/1999 | Burpee et al. | |
| 5,922,020 A | 7/1999 | Klein et al. | |
| 5,922,021 A | 7/1999 | Jang | |
| 5,925,061 A | 7/1999 | Ogi et al. | |
| 5,935,162 A | 8/1999 | Dang | |
| 5,938,697 A | 8/1999 | Killion et al. | |
| 5,948,016 A | 9/1999 | Jang | |
| 5,954,743 A | 9/1999 | Jang | |

(56) References Cited

U.S. PATENT DOCUMENTS

| | | |
|---|---|---|
| 5,980,553 A | 11/1999 | Gray et al. |
| 5,984,929 A | 11/1999 | Bashiri et al. |
| 6,001,123 A | 12/1999 | Lau |
| 6,013,854 A | 1/2000 | Moriuchi |
| 6,017,365 A | 1/2000 | VonOepen |
| 6,022,371 A | 2/2000 | Killion |
| 6,022,374 A | 2/2000 | Imran |
| 6,027,527 A | 2/2000 | Asano et al. |
| 6,042,597 A | 3/2000 | Kveen et al. |
| 6,042,606 A | 3/2000 | Frantzen |
| 6,053,941 A | 4/2000 | Lindenberg et al. |
| 6,056,775 A | 5/2000 | Borghi et al. |
| 6,059,822 A | 5/2000 | Kanesaka et al. |
| 6,068,656 A | 5/2000 | Von Oepen |
| 6,106,548 A | 8/2000 | Roubin et al. |
| 6,113,627 A | 9/2000 | Jang |
| 6,117,165 A | 9/2000 | Becker |
| 6,129,755 A | 10/2000 | Mathis et al. |
| 6,132,460 A | 10/2000 | Thompson |
| 6,132,461 A | 10/2000 | Thompson |
| 6,146,403 A | 11/2000 | St. Germain |
| 6,162,245 A | 12/2000 | Jayaraman |
| 6,168,619 B1 | 1/2001 | Dinh et al. |
| 6,183,506 B1 | 2/2001 | Penn et al. |
| 6,190,403 B1 | 2/2001 | Fischell et al. |
| 6,190,406 B1 | 2/2001 | Duerig et al. |
| 6,193,747 B1 | 2/2001 | von Oepen |
| 6,203,569 B1 | 3/2001 | Wijay |
| 6,206,911 B1 | 3/2001 | Milo |
| 6,210,429 B1 | 4/2001 | Vardi et al. |
| 6,221,099 B1 | 4/2001 | Andersen et al. |
| 6,231,598 B1 | 5/2001 | Berry et al. |
| 6,245,101 B1 | 6/2001 | Drasler et al. |
| 6,261,319 B1 | 7/2001 | Kveen et al. |
| 6,264,685 B1 | 7/2001 | Ahari |
| 6,264,688 B1 | 7/2001 | Herklotz et al. |
| 6,272,370 B1 | 8/2001 | Gillies et al. |
| 6,280,385 B1 | 8/2001 | Melzer et al. |
| 6,287,331 B1 | 9/2001 | Heath |
| 6,287,336 B1 | 9/2001 | Globerman et al. |
| 6,290,721 B1 | 9/2001 | Heath |
| 6,293,966 B1 | 9/2001 | Frantzen |
| 6,299,635 B1 | 10/2001 | Frantzen |
| 6,309,414 B1 | 10/2001 | Rolando et al. |
| 6,312,459 B1 | 11/2001 | Huang et al. |
| 6,315,791 B1 | 11/2001 | Gingras et al. |
| 6,325,825 B1 | 12/2001 | Kula et al. |
| 6,325,826 B1 | 12/2001 | Vardi et al. |
| 6,327,772 B1 | 12/2001 | Zadno-Azizi et al. |
| 6,330,884 B1 | 12/2001 | Kim |
| 6,331,188 B1 | 12/2001 | Lau et al. |
| 6,331,189 B1 | 12/2001 | Wolinsky et al. |
| 6,331,190 B1 | 12/2001 | Shokoohi et al. |
| 6,334,871 B1 | 1/2002 | Dor et al. |
| 6,336,937 B1 | 1/2002 | Vonesh et al. |
| 6,340,366 B2 | 1/2002 | Wijay |
| 6,340,367 B1 | 1/2002 | Stinson et al. |
| 6,348,065 B1 | 2/2002 | Brown et al. |
| 6,355,057 B1 | 3/2002 | DeMarais et al. |
| 6,355,058 B1 | 3/2002 | Pacetti et al. |
| 6,358,274 B1 | 3/2002 | Thompson |
| 6,361,557 B1 | 3/2002 | Gittings et al. |
| 6,361,759 B1 | 3/2002 | Frayne et al. |
| 6,379,381 B1 | 4/2002 | Hossainy et al. |
| 6,395,020 B1 | 5/2002 | Ley et al. |
| 6,402,777 B1 | 6/2002 | Globerman et al. |
| 6,423,090 B1 | 7/2002 | Hancock |
| 6,461,380 B1 | 10/2002 | Cox |
| 6,471,720 B1 | 10/2002 | Ehr et al. |
| 6,488,703 B1 | 12/2002 | Kveen et al. |
| 6,520,987 B1 | 2/2003 | Plante |
| 6,524,335 B1 | 2/2003 | Hartley et al. |
| 6,524,336 B1 | 2/2003 | Papazolgou et al. |
| 6,533,808 B1 | 3/2003 | Thompson |
| 6,540,775 B1 | 4/2003 | Fischell et al. |
| 6,540,777 B2 | 4/2003 | Stenzel |
| 6,551,351 B2 | 4/2003 | Smith et al. |
| 6,558,415 B2 | 5/2003 | Thompson |
| 6,602,282 B1 | 8/2003 | Yan |
| 6,610,086 B1 | 8/2003 | Kock et al. |
| 6,613,081 B2 | 9/2003 | Kim et al. |
| 6,629,994 B2 | 10/2003 | Gomez et al. |
| 6,652,579 B1 | 11/2003 | Cox et al. |
| 6,656,215 B1 | 12/2003 | Yanez et al. |
| 6,663,664 B1 | 12/2003 | Pacetti |
| 6,706,062 B2 | 3/2004 | Vardi et al. |
| 6,730,116 B1 | 5/2004 | Wolinsky et al. |
| 6,730,117 B1 | 5/2004 | Tseng et al. |
| 6,776,793 B2 | 8/2004 | Brown et al. |
| 6,818,014 B2 | 11/2004 | Brown et al. |
| 6,821,292 B2 | 11/2004 | Pazienza et al. |
| 6,846,323 B2 | 1/2005 | Yip et al. |
| 6,854,172 B2 | 2/2005 | Kaese et al. |
| 6,878,162 B2 | 4/2005 | Bales et al. |
| 6,962,603 B1 | 11/2005 | Brown et al. |
| 6,969,402 B2 | 11/2005 | Bales et al. |
| 6,981,986 B1 | 1/2006 | Brown et al. |
| 7,014,654 B2 | 3/2006 | Welsh et al. |
| 7,031,687 B2 | 4/2006 | Kivekas et al. |
| 7,204,848 B1 | 4/2007 | Brown et al. |
| 7,223,283 B2 | 5/2007 | Chouinard |
| 7,243,408 B2 | 7/2007 | Vietmeier |
| 7,329,277 B2 | 2/2008 | Addonizio et al. |
| 7,331,986 B2 | 2/2008 | Brown et al. |
| 7,354,450 B2 | 4/2008 | Bicek et al. |
| 7,404,823 B2 | 7/2008 | Gregorich et al. |
| 7,534,257 B2 | 5/2009 | Richter |
| 7,842,080 B2 | 11/2010 | Chouinard |
| 7,988,717 B2 | 8/2011 | Brown et al. |
| 2001/0029397 A1 | 10/2001 | Thompson |
| 2001/0039447 A1 | 11/2001 | Pinchasik et al. |
| 2001/0044652 A1 | 11/2001 | Moore |
| 2001/0056298 A1 | 12/2001 | Brown et al. |
| 2002/0007212 A1 | 1/2002 | Brown et al. |
| 2002/0022876 A1 | 2/2002 | Richter et al. |
| 2002/0055770 A1 | 5/2002 | Doran et al. |
| 2002/0095208 A1 | 7/2002 | Gregorich et al. |
| 2002/0107562 A1 | 8/2002 | Hart et al. |
| 2002/0111669 A1 | 8/2002 | Pazienza et al. |
| 2002/0116049 A1 | 8/2002 | Girton et al. |
| 2002/0120322 A1 | 8/2002 | Thompson et al. |
| 2002/0123797 A1 | 9/2002 | Majercak |
| 2002/0177893 A1 | 11/2002 | Brown et al. |
| 2003/0004567 A1 | 1/2003 | Boyle et al. |
| 2003/0018380 A1 | 1/2003 | Craig et al. |
| 2003/0055485 A1 | 3/2003 | Lee et al. |
| 2003/0176914 A1 | 9/2003 | Rabkin et al. |
| 2003/0195606 A1 | 10/2003 | Davidson et al. |
| 2003/0225448 A1 | 12/2003 | Gerberding |
| 2004/0002753 A1 | 1/2004 | Burgermeister et al. |
| 2004/0034402 A1 | 2/2004 | Bales et al. |
| 2004/0044401 A1 | 3/2004 | Bales et al. |
| 2004/0073291 A1 | 4/2004 | Brown et al. |
| 2004/0088039 A1 | 5/2004 | Lee et al. |
| 2004/0088044 A1 | 5/2004 | Brown et al. |
| 2004/0111147 A1 | 6/2004 | Rabkin et al. |
| 2004/0117002 A1 | 6/2004 | Girton et al. |
| 2004/0143318 A1 | 7/2004 | Tseng et al. |
| 2004/0204751 A1 | 10/2004 | Fischell et al. |
| 2005/0060025 A1 | 3/2005 | Mackiewicz et al. |
| 2005/0125051 A1 | 6/2005 | Eidenschink et al. |
| 2005/0149168 A1 | 7/2005 | Gregorich |
| 2006/0015173 A1 | 1/2006 | Clifford et al. |
| 2006/0052864 A1 | 3/2006 | Harder et al. |
| 2006/0271159 A1 | 11/2006 | Gregorich et al. |
| 2007/0150048 A1 | 6/2007 | Tischler |
| 2007/0219624 A1 | 9/2007 | Brown et al. |
| 2008/0097579 A1 | 4/2008 | Shanley et al. |
| 2008/0221661 A1 | 9/2008 | Bidne et al. |
| 2009/0163994 A1 | 6/2009 | Quigley et al. |
| 2010/0100166 A1 | 4/2010 | Richter et al. |
| 2012/0172972 A1 | 7/2012 | Meyer et al. |
| 2012/0226346 A1 | 9/2012 | Boismier et al. |

(56) References Cited

U.S. PATENT DOCUMENTS

FOREIGN PATENT DOCUMENTS

| | | |
|---|---|---|
| DE | 29701758 | 5/1997 |
| DE | 29708689 | 7/1997 |
| DE | 29708879 | 7/1997 |
| DE | 29716476 | 12/1997 |
| DE | 29816878 | 12/1998 |
| EP | 0364737 | 4/1990 |
| EP | 0364787 | 4/1990 |
| EP | 0540290 | 5/1993 |
| EP | 0541443 | 5/1993 |
| EP | 0606165 | 7/1994 |
| EP | 0679372 | 11/1995 |
| EP | 0796597 | 9/1997 |
| EP | 0800801 | 10/1997 |
| EP | 0801933 | 10/1997 |
| EP | 0821920 | 2/1998 |
| EP | 0876806 | 11/1998 |
| EP | 0897698 | 2/1999 |
| EP | 0970664 | 1/2000 |
| EP | 0983753 | 3/2000 |
| EP | 1034751 | 9/2000 |
| EP | 1159934 | 12/2001 |
| EP | 1190685 | 3/2002 |
| EP | 1362564 | 11/2003 |
| JP | 6004175 | 3/1994 |
| JP | 6181993 | 7/1994 |
| WO | 9417754 | 8/1994 |
| WO | 9621404 | 7/1996 |
| WO | 9626689 | 9/1996 |
| WO | 9628116 | 9/1996 |
| WO | 9704721 | 2/1997 |
| WO | 9714375 | 4/1997 |
| WO | 9725937 | 7/1997 |
| WO | 9732543 | 9/1997 |
| WO | 9732544 | 9/1997 |
| WO | 9733534 | 9/1997 |
| WO | 9740780 | 11/1997 |
| WO | 9740781 | 11/1997 |
| WO | 9740782 | 11/1997 |
| WO | 9740783 | 11/1997 |
| WO | 9740784 | 11/1997 |
| WO | 9740874 | 11/1997 |
| WO | 9745073 | 12/1997 |
| WO | 9820810 | 5/1998 |
| WO | 9826732 | 6/1998 |
| WO | 9837833 | 9/1998 |
| WO | 9847447 | 10/1998 |
| WO | 9925273 | 5/1999 |
| WO | 9944535 | 9/1999 |
| WO | 0030563 | 6/2000 |
| WO | 0132099 | 5/2001 |
| WO | 0158386 | 8/2001 |
| WO | 02060344 | 8/2002 |
| WO | 2004032802 | 4/2004 |
| WO | 2008005535 | 1/2008 |

OTHER PUBLICATIONS

Beyar et al "Newer Stents; Material and Designs" IAGS Proceedings 9(5): 363-371 (Jun. 1997).

Brochure Entitled Ave Micro Stent TM, Instructions for Use, by Applied Vascular Engineering, Inc., pp. 1-15.
Brochure Entitled "Micro Stent TM", By Applied Vascular Engineering, Inc.
Brochure from Cook Incorporated regarding Gianturco-Rosch Biliary Z-Stents TM, 1989.
Cambridge Dictionary of Science and Technology, Cambridge University Pres. 128, Date Unknown.
Expandable Biliary Endoprosthesis: An Experimental Study, by Carrasco et al., AJR vol. 145, Dec. 1985, pp. 1279-1282.
Self-Expanding Stainless Street Biliary Stents, by Harold G. Coons, MD, Radiology 1989, vol. 170, No. 3 part 2, pp. 979-983.
Gianturco Expandable Metallic Biliary Stents: Results of a European Clinical Trial, by Irving, et al Interventional Radiology, vol. 172, No. 2, Aug. 1989, pp. 321-326.
Japanese Infringements Search on Articulated Expandable Stents, dated Jul. 12, 1995.
Manufacturing Processes for Engineering Materials, by Serope Kalpallian, Illinois Institute of Technology, Addison - Wesley Publishing Company, pp. 340, Date Unknown.
Improved Dilation Catheter Balloons, by Stanley B. Levy PhD., Journal of Clinical Engineering, vol. 11, No. 4, Jul.-Aug. 1986, pp. 291-296.
Engineering Fluid Mechanics, Third Edition, John A. Roberson and Clayton T Crowe, pp. 94 and pp. 414-421, Date Unknown.
Roguin et al Acute and 30 - Day Results of the Serpentine Balloon Expandable Stent Implantation in Simple and Complex Coronary Arterial Narrowing\, The American Journal of Cardiology, 80: 1155-1162 (Nov. 1997).
Roguin et al, "BeStent—the serpentine balloon expandable stent; review of mechanical properties and clinical experience", Astif Organs, 22(3):243-249 (Mar. 1998).
A View of Vascular Stents, by Richard A. Schatz, MD, From the Arizona Heart Institute Foundation , Phoenix, Arizona, Circulation: vol. 79, No. 2, Feb. 1989, pp. 445-457.
The Self-Expanding Mesh Stent, by Ulrich Sigwart, Section IV Chapter 29, pp. 605-610.
SMART TM Stent Brochure, Cordis, a Johnson & Johnson company Copyright 1998.
Starck, E., "First Clinical Experience with the Mernotherrn Vascular Stent", STENTS State of the Art Future Development, pp. 59-62 (Jun. 1995).
Technical Note Entitled Modifications of Gianturco Expandable Wire Stents, by Barry T. Uchida et al., AJR, vol. 150, May 1988, pp, 1185-1187.
Tracheobronchial Tree: Expandable Metallic Stents Used in Experimental and Clinical Applications\, Work in Progress, by Wallace et al, Radiology, Feb. 1986, pp. 309-312.
U.S. Appl. No. 08/396,569, Brown, filed Mar. 1, 1995.
U.S. Appl. No. 60/076,946, filed Mar. 5, 1998, Tseng et al.
U.S. Appl. No. 10/474,848, Tseng et al., filed Dec. 29, 2003.
International Search Report and Written Opinion, PCT/US2011/052622, mailed Dec. 6, 2011.
Melzer, A. et al., Performance Improvement of Surgical Instrumental Through the Use of Ni-Ti Materials, Proceedings of SMST-94 The First International conference on Shape Memory and Superelastic Technologies, pp. 401-409 (Mar. 7-10, 1994).

\* cited by examiner

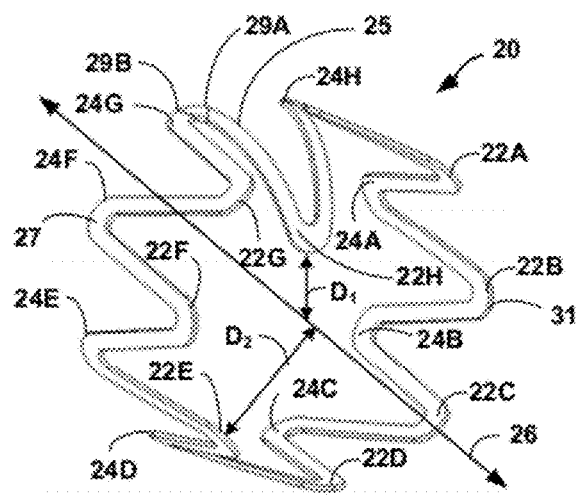
FIG. 2A
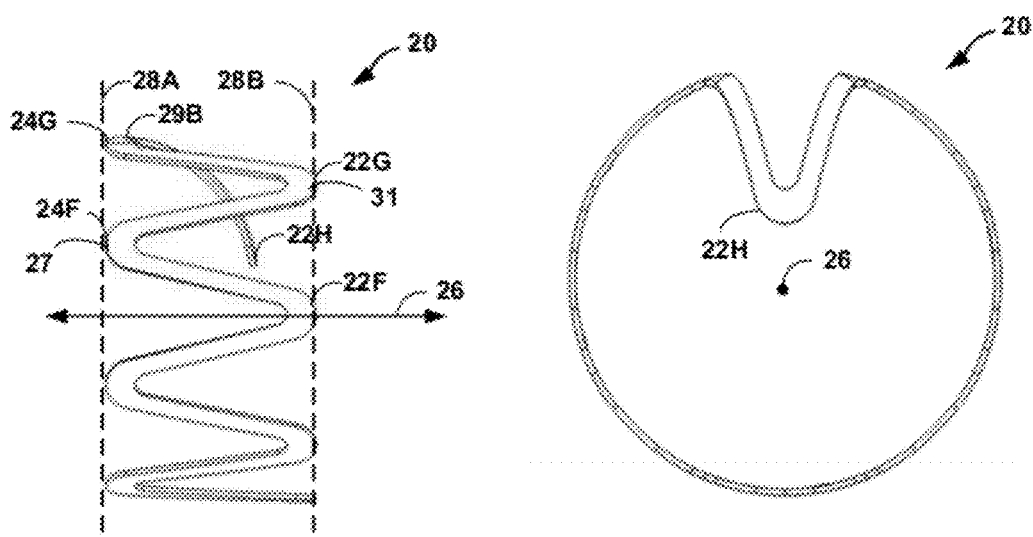
FIG. 2B
FIG. 2C

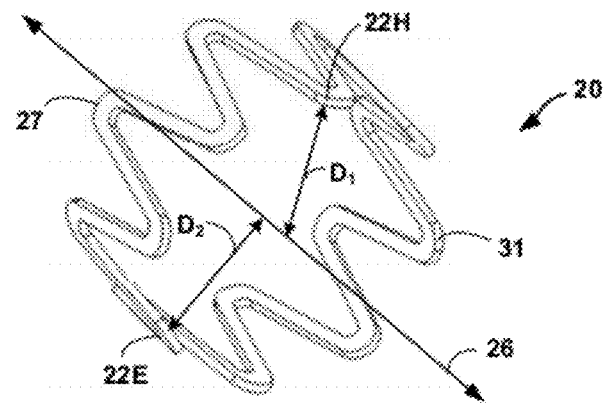
FIG. 3A
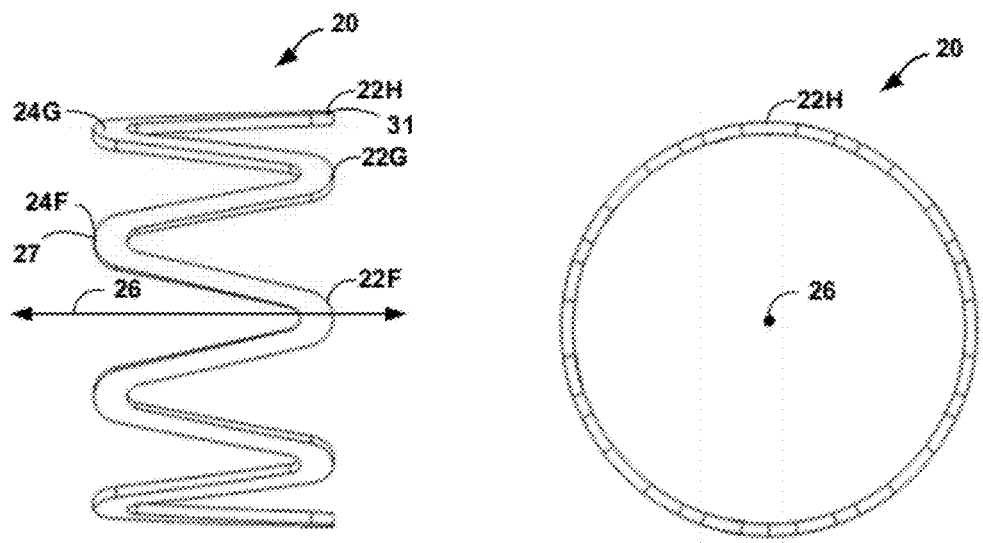
FIG. 3B  FIG. 3C

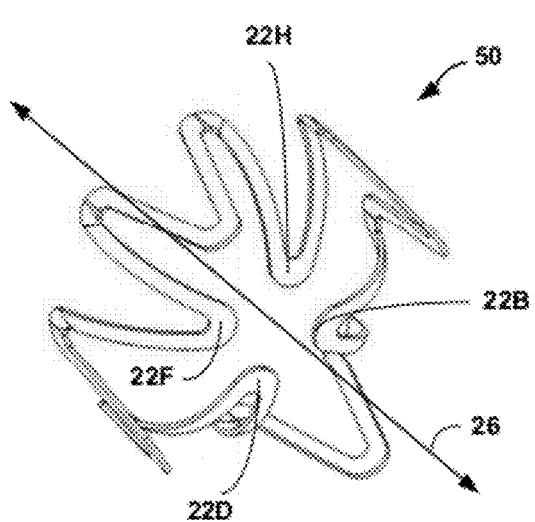 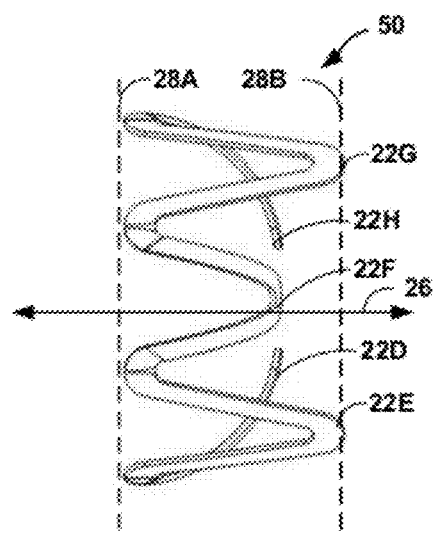
FIG. 5A  FIG. 5B
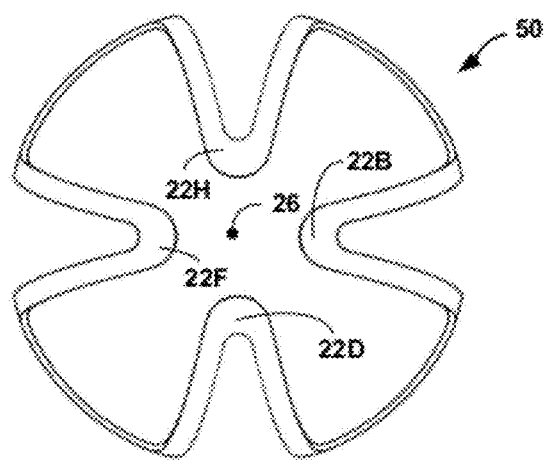
FIG. 5C

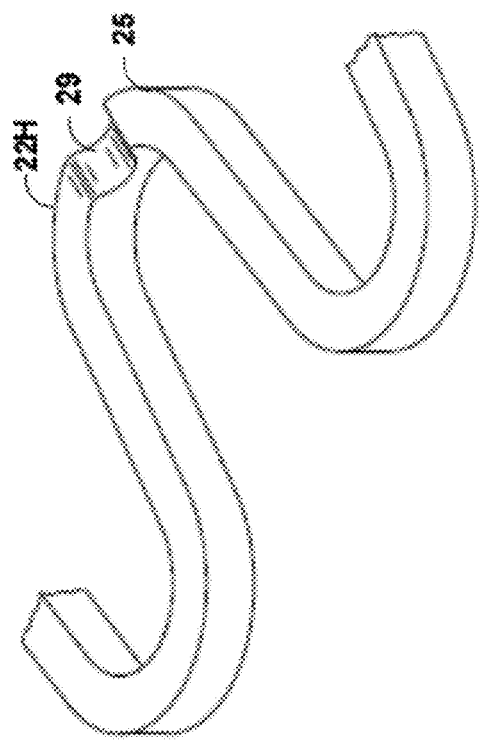
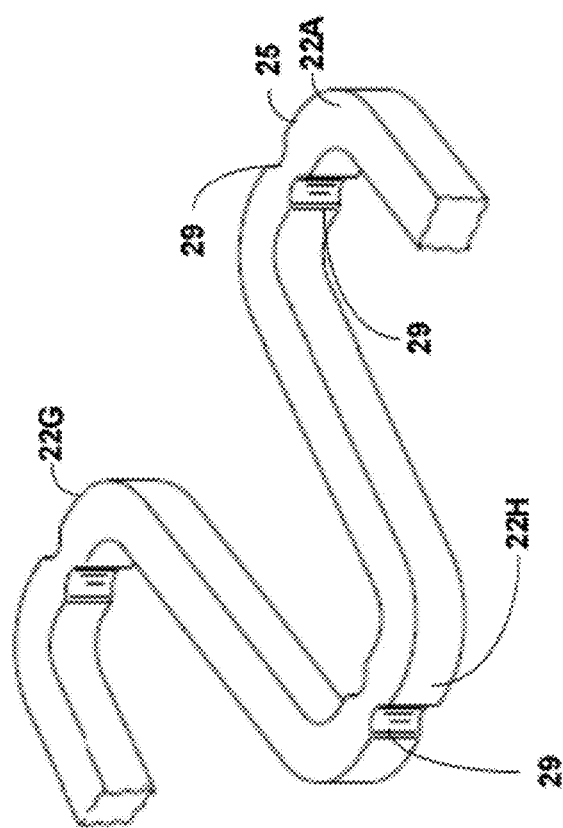
FIG. 6B
FIG. 6A

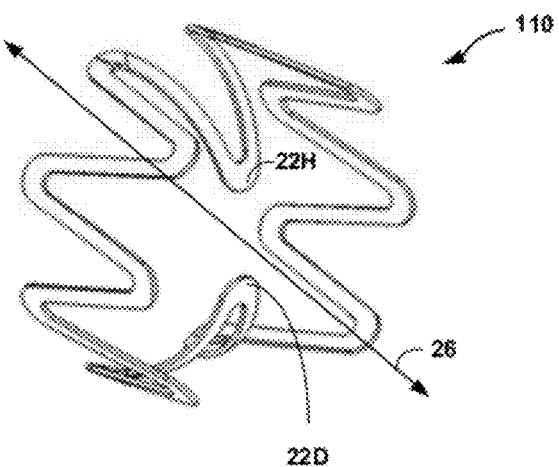
FIG. 10A
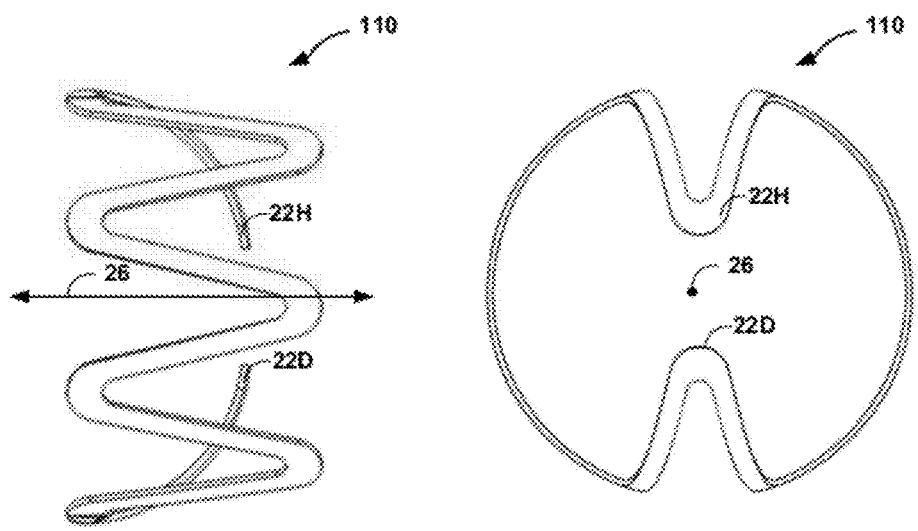
FIG. 10B
FIG. 10C

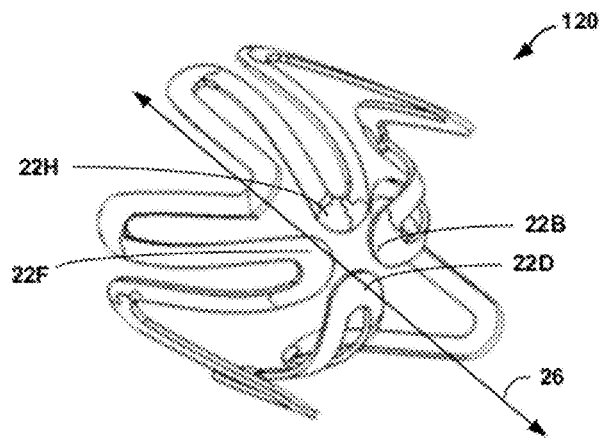
FIG. 11A
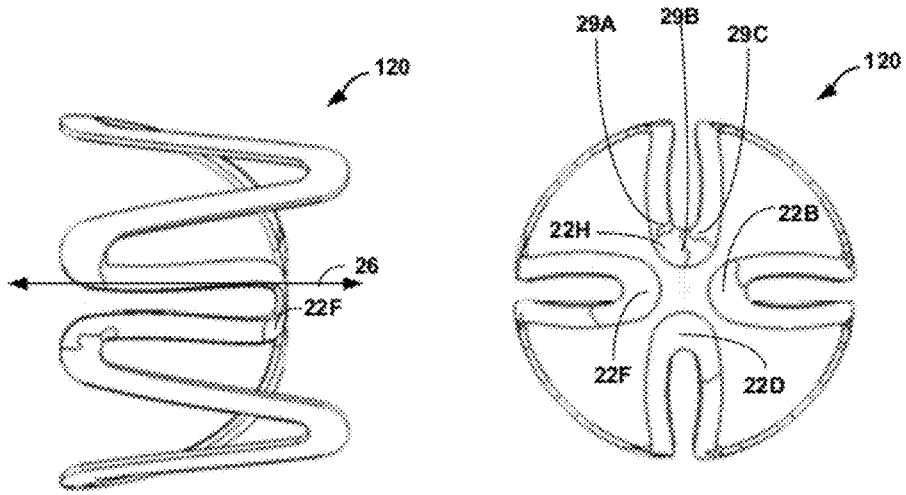
FIG. 11B
FIG. 11C

STENT WITH REDUCED PROFILE

TECHNICAL FIELD

The disclosure relates to endoprosthesis devices for implantation within a body vessel and delivery systems for delivering such devices.

BACKGROUND

A stent is a medical device introduced to a body lumen and is well known in the art. Typically, a stent is implanted in a blood vessel at the site of a stenosis or aneurysm endoluminally, i.e., by so-called "minimally invasive techniques" in which the stent in a radially reduced configuration, optionally restrained in a radially compressed configuration by a sheath and/or catheter, is delivered by a stent delivery system or "introducer" to the site where it is required. The introducer may enter the body from an access location outside the body, such as through the patient's skin, or by a "cut down" technique in which the entry blood vessel is exposed by minor surgical means.

Stents, grafts, stent-grafts, vena cava filters, expandable frameworks, and similar implantable medical devices are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, fallopian tubes, coronary vessels, secondary vessels, etc. They may be self-expanding, expanded by an internal radial force, such as when mounted on a balloon, or a combination of self-expanding and balloon expandable (hybrid expandable).

SUMMARY

In general, this disclosure describes medical devices, systems, and techniques that allow portions of a stent to be folded within a balloon of a stent delivery system. In particular, the various medical devices, systems, and techniques described throughout this disclosure allow one or more peaks and/or troughs of a stent to be folded into a balloon fold of a pleated delivery balloon. In this manner, a profile of the stent can be reduced when the stent is crimped onto the balloon.

In one example, the disclosure is directed to a stent delivery system comprising a catheter comprising an expandable balloon, the balloon having a pleated state and an unpleated state, the balloon having at least two pleats in the pleated state, adjacent pleats of a balloon being separated by a fold in the pleated state, and a stent having a reduced state and an expanded state. The stent comprises a plurality of interconnected annular rings arranged about a longitudinal axis, each of the plurality of annular bands comprising a plurality of peaks and a plurality of troughs, wherein in the reduced state and positioned on the balloon, at least one of the plurality of peaks of at least one of the plurality of rings extends into a fold of the balloon in the pleated state, the at least one peak being positioned a first distance from the longitudinal axis, another one of the plurality of peaks being positioned a second distance from the longitudinal axis, the first distance being less than the second distance, and wherein in the expanded state, the plurality of peaks of the stent being positioned at substantially the same distance from the longitudinal axis.

In another example, the disclosure is directed to a stent having a reduced state and an expanded state, the stent comprising a plurality of interconnected annular rings arranged about a longitudinal axis, each of the plurality of annular bands comprising a plurality of peaks and a plurality of troughs, wherein in the reduced state, at least one of the plurality of peaks of at least one of the plurality of rings is positioned a first distance from the longitudinal axis, another one of the plurality of peaks being positioned a second distance from the longitudinal axis, the first distance being less than the second distance, and wherein in the expanded state, the plurality of peaks of the stent being positioned at substantially the same distance from the longitudinal axis.

The details of one or more aspects of the disclosure are set forth in the accompanying drawings and the description below. Other features, objects, and advantages will be apparent from the description and drawings, and from the claims.

BRIEF DESCRIPTION OF DRAWINGS

FIG. 2A is an isometric view of one example annular ring of a stent that can be used to implement various techniques of this disclosure.

FIG. 2B is a side view of the example annular ring depicted in FIG. 2A.

FIG. 2C is an end view of the example annular ring depicted in FIG. 2A.

FIG. 3A is an isometric view of the example annular ring depicted in FIG. 2A in an expanded state.

FIG. 3B is a side view of the example annular ring depicted in FIG. 3A.

FIG. 3C is an end view of the example annular ring depicted in FIG. 3A.

FIG. 5A is an isometric view of another example annular ring of a stent that can be used to implement various techniques of this disclosure.

FIG. 5B is a side view of the example annular ring depicted in FIG. 4A.

FIG. 5C is an end view of the example annular ring depicted in FIG. 4A.

FIG. 6A is a perspective view of one example of a portion of an annular ring.

FIG. 6B is a perspective view of another example of a portion of an annular ring.

FIG. 10A is an isometric view of another example annular ring of a stent that can be used to implement various techniques of this disclosure.

FIG. 10B is a side view of the example annular ring depicted in FIG. 10A.

FIG. 10C is an end view of the example annular ring depicted in FIG. 10A.

FIG. 11A is an isometric view of another example annular ring of a stent that can be used to implement various techniques of this disclosure.

FIG. 11B is a side view of the example annular ring depicted in FIG. 11A.

FIG. 11C is an end view of the example annular ring depicted in FIG. 11A.

DETAILED DESCRIPTION

This disclosure describes medical devices, systems, and techniques that allow portions of a stent to be folded into a balloon fold of a delivery balloon. As such, using certain techniques of this disclosure, a portion of the stent can be embedded within a fold of the delivery balloon during the folding process. Embedding a portion of the stent within a fold of the balloon provides one or more advantages over designs that do not utilize such techniques. For example, embedding a portion of the stent within a fold of the balloon reduces the profile of the stent in a crimped state. In addition, embedding a portion of the stent within a fold of the balloon helps secure the stent to the balloon.

Figure 1:
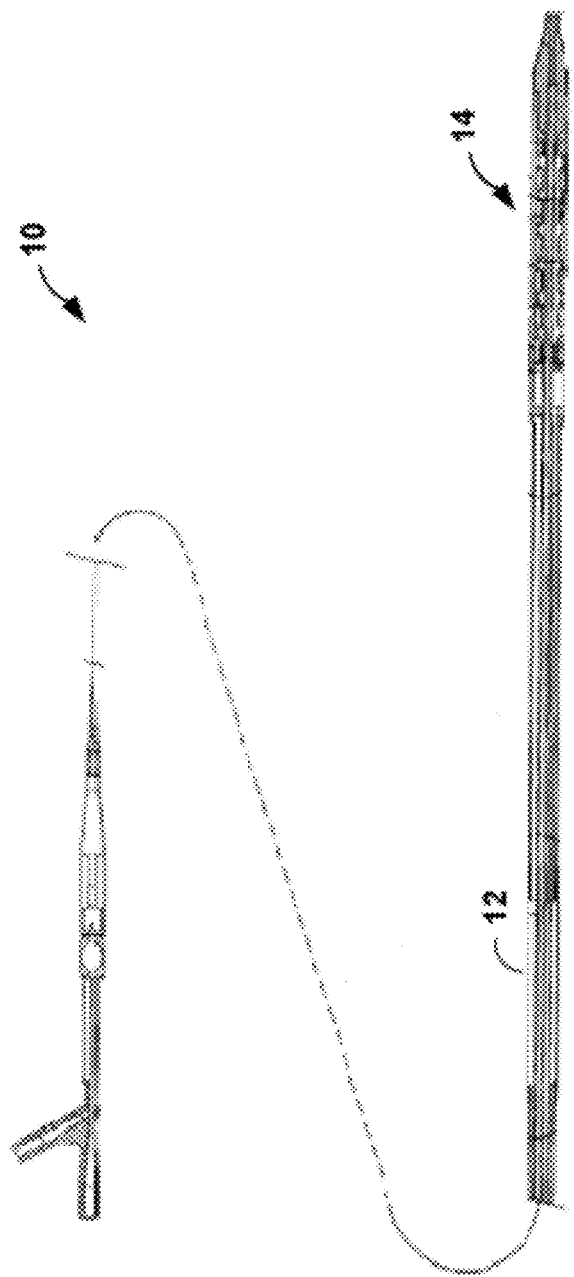
FIG. 1 is a side view of a stent delivery system that may be used in accordance with various techniques of this disclosure.

FIG. 1 is a side view of a stent delivery system that may be used in accordance with various techniques of this disclosure. As seen in FIG. 1, stent delivery system 10 includes a catheter 12 having distal end 14 upon which a delivery balloon and stent may be secured in order to deliver the stent to a site within a patient's body. Stent delivery systems such as stent delivery system 10 are well known and, for purposes of conciseness, will not be described in detail in this disclosure.

FIG. 2A is an isometric view of one example annular ring of a stent that can be used to implement various techniques of this disclosure. In particular, the example annular ring of FIG. 2A, shown generally at 20, includes a plurality of peaks 22A-22G (collectively referred to in this disclosure as "peaks 22") and a plurality of troughs 24A-24G (collectively referred to in this disclosure as "troughs 24") created by interconnected struts 25. As seen in FIG. 2A, annular band 20 is arranged about longitudinal axis 26 and defines a cylindrical volume, represented by dashed lines 28A and 28B in FIG. 2B (collectively referred to in this disclosure as "lines 28"). The cylindrical volume is defined by the unbent peaks 22 and troughs 24 of annular ring 20. Additionally, line 28A defines a proximal end of annular band 20 and line 28B defines a distal end of annular band 20.

In accordance with this disclosure, at least one of the peaks and/or troughs of an annular ring of a stent is configured to bend inward into the cylindrical volume defined by the ring and into a balloon fold of a balloon, i.e., the space between adjacent pleats of a pleated balloon. In FIG. 2A, peak 22H of ring 20 bends inward into the cylindrical volume defined by the ring. Although not depicted in FIG. 2A, peak 22H bends into a balloon fold when placed onto a pleated delivery balloon. In this manner, when in a reduced state and positioned on the balloon, a first proximal end of at least one of the plurality of peaks or troughs of the stent extends into a fold of the balloon in the pleated state, the at least one peak being positioned a first distance from the longitudinal axis, another one of the plurality of peaks being positioned a second distance from the longitudinal axis, the first distance being less than the second distance.

Each of the plurality of rings 20 has a respective proximal end 27 and a respective distal end 31. In accordance with certain techniques of this disclosure, when a stent is in a reduced state, and thus when ring 20 is in a reduced state, as shown in FIGS. 2A-2C, one or more of the plurality of peaks of the stent, e.g., bent peak 22H, is positioned such that bent peak 22H is a first distance from longitudinal axis 26, e.g., distance $D_1$, and another one of the plurality of peaks, e.g., unbent peak 22E, is positioned a second distance from longitudinal axis 26, e.g., distance $D_2$, where the first distance, e.g., distance $D_1$, is less than the second distance, e.g., distance $D_2$. In this manner, one or more of the plurality of peaks of the stent extends into a fold of a balloon in a pleated state. That is, when the example configuration depicted in FIG. 2A is positioned on a pleated balloon, bent peak 22H extends into a fold of the balloon (e.g., fold 46 of balloon 30 in FIG. 4B).

In some example configurations, both a peak and a trough can be bent to extend into a fold of a pleated balloon. For example, in addition to peak 22H of FIG. 2A being bent and thus positioned at a distance from longitudinal axis 26 that is greater than the distance of unbent peaks, e.g., unbent peak 22E, from longitudinal axis 26, a trough of ring 20 can similarly be bent inward. For example, when a stent is in a reduced state, trough 24E can be bent inward such that it is positioned at a third distance from longitudinal axis 26 while unbent troughs, e.g., trough 24B, are positioned at a fourth distance from longitudinal axis 26, where the third distance is less than the fourth distance. In this manner, a ring can include at least one bent peak and at least one bent trough.

As shown and described in more detail below, configuring at least one peak and/or trough of a ring of a stent to bend inward into a balloon fold reduces the profile of the stent after crimping by minimizing the number of peaks (or troughs) that can interfere with another peak (or trough) during the crimping process. A stent can only be crimped to the point that its peaks or troughs begin to touch one another, thereby limiting the extent to which the stent's size can be reduced by crimping. In accordance with this disclosure, by bending one or more peaks and/or troughs of one or more annular rings of a stent into a balloon fold prior to crimping, the peaks and/or troughs are essentially eliminated from the circumference of the stent. In this manner, the stent can be crimped to a smaller size than would otherwise be achievable, thereby reducing the profile of the stent.

A peak or trough of a ring, e.g., peak 22H of ring 20, can be configured to bend inward and extend into a balloon fold of a balloon using various techniques in accordance with this disclosure. In one example, peaks or troughs of a ring, e.g., peak 22H of ring 20, are bent inward by folding the peak(s) or trough(s) at particular portions of struts 25. These portions of struts 25, referred to as fold lines, are depicted in FIG. 2A at 29A and 29B (referred to generally in this disclosure as "fold lines 29"). Although only two fold lines 29A and 29B are depicted in FIG. 2A, annular ring 20 can have more fold lines 29 or only a single fold line 29. As seen in FIG. 2A, peak 22H of ring 20 is bent inward into the cylindrical volume defined by ring 20 by folding at fold lines 29A, 29B, as indicated by the fact that the struts adjacent trough 24G are closer to each other than struts adjacent other troughs of ring 20, e.g., trough 24F.

Peaks or troughs of a ring can be folded at fold lines 29 using various techniques in accordance with this disclosure. In one example, the material at one or more portions of one or more struts of a ring can be reduced in order to create portion(s) that are thinner than the remainder of the strut. For example, in FIG. 2A, material near fold line 29A and/or fold line 29B can be reduced such that a width of strut 25 is thinner near the fold line than elsewhere along on the strut. As another example, in FIG. 2A, material near fold line 29A and/or fold line 29B can be reduced such that a thickness of strut 25 is thinner near the fold line than elsewhere along on the strut. The strut can be formed by laser cutting, chemical etching, electroforming or stamping of a tube. In this manner, the geometry of the stent can be configured to allow peaks and/or troughs to be folded. These techniques are shown and described in more detail below with respect to FIGS. 6A and 6B.

In another example folding technique, rather than configuring the geometry of the stent to allow peaks and/or troughs to be folded in the manner described throughout this disclosure, crimping techniques are employed instead. In accordance with this disclosure, crimping techniques are used that bend one or more peaks and/or troughs inward into the cylindrical volume defined by the ring and into a balloon fold of a balloon. In one example crimping process, a mold is employed, e.g., a clamshell mold, that includes pins that push certain portions of a stent below other portions as the mold is closed in order to bent certain peaks into folds of the balloon.

Any suitable stent material may be used in the manufacture of the rings and stents described in this disclosure. Examples of such materials include metals such as stainless steel, tantalum, elgiloy and shape memory metals such as nitinol and shape memory polymers. The rings and stents may also be made of suitable polymeric materials.

FIG. 2B is a side view of the example annular ring 20 depicted in FIG. 2A. Specifically, FIG. 2B depicts ring 20 arranged about longitudinal axis 26 and having a peak, namely peak 22H, bending inward into the cylindrical volume defined by the ring, represented by dashed lines 28.

FIG. 2C is an end view of the example annular ring 20 depicted in FIG. 2A. In particular, FIG. 2C depicts ring 20 arranged about longitudinal axis 26 and having a peak, namely peak 22H, bending inward into the cylindrical volume defined by the ring (not shown in FIG. 2B).

FIG. 3A is an isometric view of the example annular ring depicted in FIG. 2A in an expanded state. In the expanded state, peak 22H (which was previously bent in FIG. 2A) has expanded outwardly away from longitudinal axis 26 such that peak 22h is positioned at substantially the same distance from longitudinal axis 26 as previously unbent peaks, e.g., peak 22E. In other words, in FIG. 3A, $D_1$ and $D_2$ are approximately equal. FIGS. 3B and 3C are side and end views, respectively, of the example annular ring depicted in FIG. 3A.

Figure 4B:
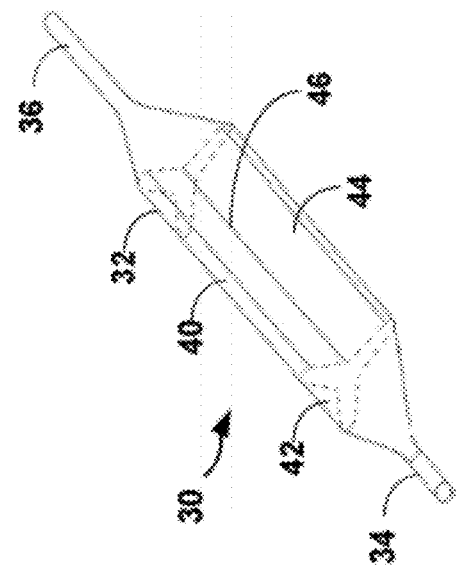
FIGS. 4A-4B are perspective views of a balloon in an unpleated state and a pleated state, respectively, that may be used in conjunction with the stent delivery system shown in FIG. 1.
Figure 4A:
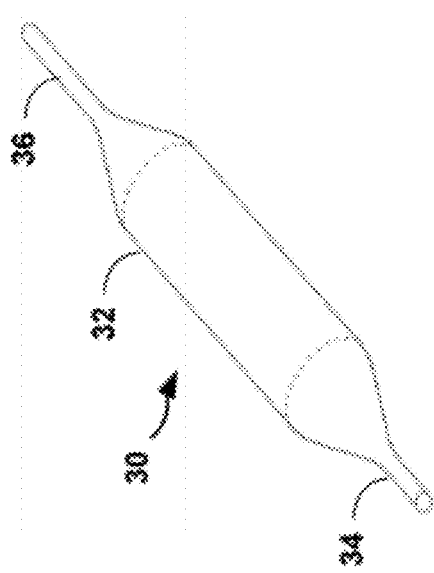

FIGS. 4A-4B are perspective views of a delivery balloon in an unpleated state and a pleated state, respectively, that can be used in conjunction with the stent delivery system shown in FIG. 1. In FIG. 4A, delivery balloon 30 with balloon body 32, shown in an unpleated, or expanded state, can be secured to distal end 14 of catheter 12 (FIG. 1), e.g., by adhesive attachment of proximal end 34 of balloon 30 to an outer shaft of catheter 12 and distal end 36 of balloon 30 to an inner shaft of catheter 12.

FIG. 4B depicts delivery balloon 30 with balloon body 32 in a pleated state, prior to folding of the balloon. As depicted in FIG. 4B, balloon body 32 includes three pleats, namely pleats 40, 42, and 44. In other configurations, balloon body 32 includes fewer or more pleats. The balloon body, or balloon, has at least two pleats in the pleated state.

As mentioned above, using certain techniques of this disclosure, at least one of the peaks of an annular ring of a stent is configured to bend inward into the cylindrical volume defined by the ring and into a balloon fold of a balloon. In one example, a balloon fold is the area or space between adjacent pleats on a balloon. By way of specific example, FIG. 4B depicts balloon 30 having balloon fold 46 located between adjacent pleats 40, 44. Similarly, balloon 30 has two other balloon folds (not shown) located between adjacent pleats 40, 42 and adjacent pleats 42, 44. By configuring at least one peak of annular rings of a stent, e.g., peak 22H of annular ring 30 of FIGS. 2A-2C, to bend inward into the cylindrical volume defined by the ring and into a balloon fold of a balloon, e.g., balloon fold 46 of balloon 30 of FIG. 4B, the profile of the stent is reduced in a crimped state. The combination of a stent and balloon is shown and described in detail below with respect to FIGS. 7A and 8A.

FIG. 5A is an isometric view of another example annular ring of a stent that can be used to implement various techniques of this disclosure. In particular, FIG. 5A depicts annular ring 50 arranged about longitudinal axis 26 and configured to have four peaks that bend inward into a cylindrical volume defined by ring 50 and into a balloon fold of a balloon. In FIG. 5A, peaks 22B, 22D, 22F, and 22H of ring 20 bend inwards into the cylindrical volume defined by the ring. As shown below in FIG. 6, peaks 22B, 22D, 22F, and 22H bend into a balloon fold when placed onto a pleated delivery balloon. FIGS. 5B and 5C depict a side view and an end view, respectively, of the example annular ring depicted in FIG. 5A.

FIG. 6A is a perspective view of one example of a portion of an annular ring. In particular, FIG. 6A depicts fold lines 29 in a portion of an annular ring, e.g., annular rings 20 or 50. In the example configuration depicted in FIG. 6A, fold lines 29 are formed by reducing a portion of the thickness of strut 25, e.g., a notch in strut 25, in the bend area. By reducing a portion of the thickness of strut 25, peaks 22A and 22G can be compressed toward each other, thereby allowing peak 22H to be bent so that it extends into a fold of a pleated balloon.

FIG. 6B is a perspective view of another example of a portion of an annular ring. In particular, FIG. 6B depicts fold lines 29 in a portion of an annular ring, e.g., annular rings 20 or 50. In the example configuration depicted in FIG. 6B, fold lines 29 are formed by reducing a portion of the width of strut 25, e.g., a notch in strut 25, in the bend area. By reducing a portion of the width of strut 25, peak 22H can be compressed and bent so that it extends into a fold of a pleated balloon.

In other example configurations, strut(s) 25 can be formed into a bent shape. In such an example configuration, the bent shape reduces or eliminates the need for a notch or other reduction in a portion of strut 25.

Figures 7A, 7B:
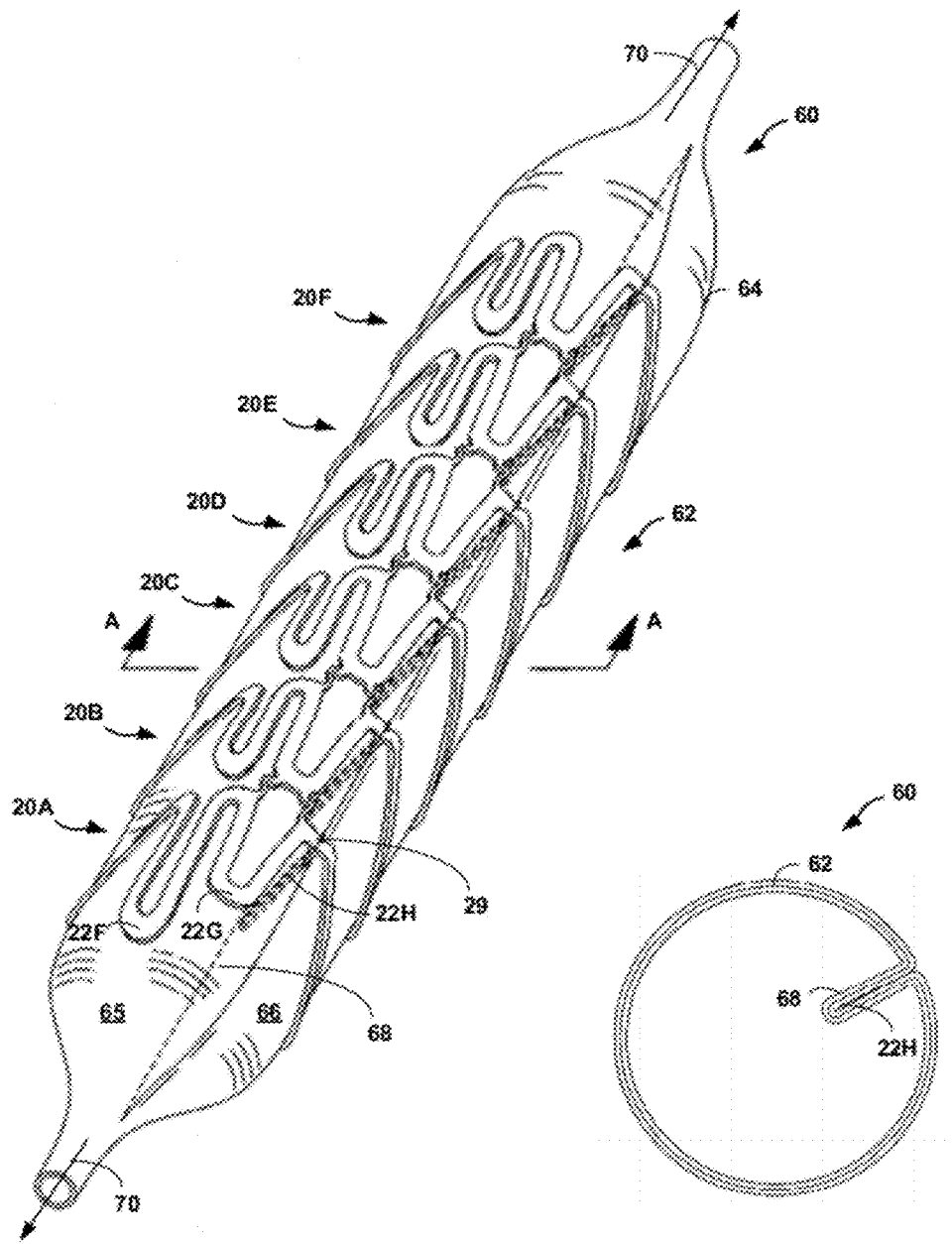
FIG. 7A is a perspective view of an example stent for use with a pleated balloon, in accordance with this disclosure.
FIG. 7B is a cross-sectional view of the example stent and balloon depicted in FIG. 6A.

FIG. 7A is a perspective view of an example stent for use with a pleated balloon, in accordance with this disclosure. In particular, FIG. 7A depicts a stent delivery system, shown generally at 60, that comprises a stent, shown generally at 62, having a plurality of interconnected annular rings 20A-20F, e.g., annular rings 20 of FIGS. 2A-2C, positioned on expandable balloon 64 and arranged about a longitudinal axis, shown generally at 70. Balloon 64 is depicted in a pleated state and includes adjacent pleats 65 and 66. Adjacent pleats 65, 66 are separated by fold 68.

Stent 62, depicted in a reduced in FIG. 7A, includes at least one peak, namely peak 22H, extending into fold 68 of pleated balloon 64. Peak 22H of ring 20A, for example, extends into fold 68 by being bent inward along fold line 29. As shown and described above in detail with respect to FIGS. 2A-2C, at least one of annular bands 20 of stent 62 includes a peak, e.g., peak 22H, positioned a first distance from longitudinal axis 70 and another peak, e.g., peak 22G, positioned a second distance from longitudinal axis 70, the first distance being less than the second distance. When stent 62 is in an expanded state, the plurality of peaks 22 of stent 62 are positioned at substantially the same distance from longitudinal axis 70, as shown and described above with respect to FIGS. 3A-3C. FIG. 7B is a cross-sectional view of the example stent and balloon depicted in FIG. 7A, taken along line A-A.

In this manner, a portion of stent 62 is embedded within a fold of the balloon, thereby reducing the profile of stent 62 in a reduced or crimped state. In addition, embedding a portion of the stent within a fold of the balloon helps secure the stent to the balloon.

Although stent 62 is depicted as having six rings 20A-20F, stent 62 is not limited to such a configuration. Rather, stent 62 can have more or fewer rings 20. Additionally, although pleated balloon 64 is depicted as having two adjacent pleats and a fold in between, balloon 64 can have more pleats, and thus more folds, thereby allowing more peaks in a ring to be extend into folds. Further, it should be noted that although each of rings 20A-20F includes a peak that extends into fold 68 of balloon 64, the disclosure is not so limited. Rather, in some examples, only one ring, e.g., ring 20A, of stent 62 includes a bent peak that extends into a fold. In other example configurations, multiple rings 20 of stent 62, but less than all rings 20, include a bent peak that extends into a fold.

Figures 8A, 8B:
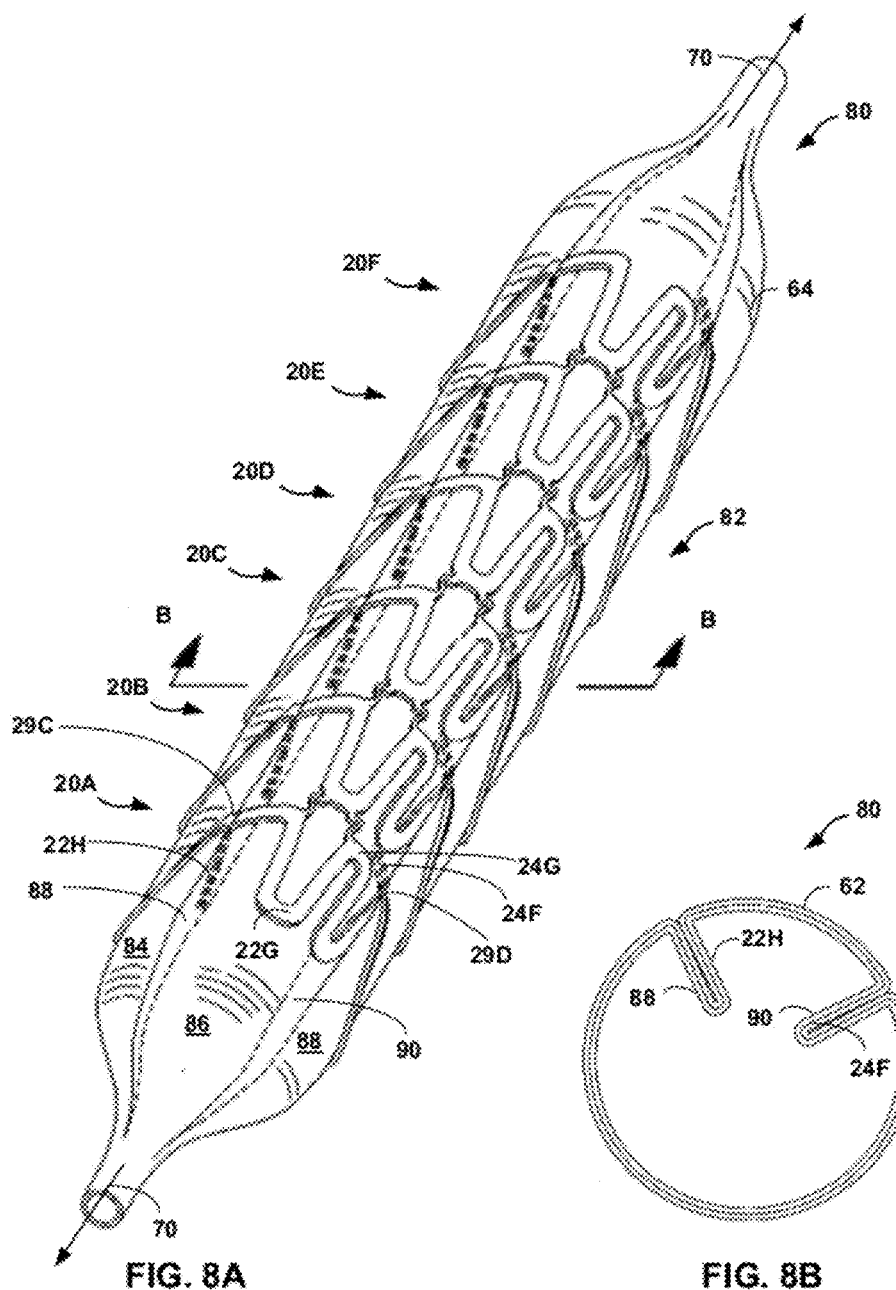
FIG. 8A is a perspective view of another example stent for use with a pleated balloon, in accordance with this disclosure.
FIG. 8B is a cross-sectional view of the example stent and balloon depicted in FIG. 7A.

FIG. 8A is a perspective view of another example stent for use with a pleated balloon, in accordance with this disclosure. In particular, FIG. 8A depicts a stent delivery system, shown generally at 80, that comprises a stent, shown generally at 82, having a plurality of interconnected annular rings 20A-20F, e.g., annular rings 20 of FIGS. 2A-2C, positioned on expandable balloon 64 and arranged about a longitudinal axis, shown generally at 70. Balloon 64 is depicted in a pleated state and includes pleats 84, 86, and 88. Adjacent pleats 84, 86 are separated by fold 88 and adjacent pleats 86, 88 are separated by fold 90.

Stent 82, depicted in a reduced in FIG. 8A, includes at least one peak, namely peak 22H, extending into fold 88 of pleated balloon 64. Peak 22H of ring 20A, for example, extends into fold 88 by being bent inward along fold line 29C. As shown and described above in detail with respect to FIGS. 2A-2C, at least one of annular bands 20 of stent 82 includes a peak, e.g., peak 22H, positioned a first distance from longitudinal axis 70 and another peak, e.g., peak 22G, positioned a second distance from longitudinal axis 70, the first distance being less than the second distance. When stent 62 is in an expanded state, the plurality of peaks 22 of stent 82 are positioned at substantially the same distance from longitudinal axis 70, as shown and described above with respect to FIGS. 3A-3C.

In addition, in the example shown in FIG. 8A, at least one of annular bands 20 of stent 82 includes a trough, e.g., trough 24F, that extends into a fold, e.g., fold 88, of pleated balloon 64. Trough 24F is positioned a third distance from longitudinal axis 70 and another trough, e.g., trough 24G, is positioned a fourth distance from longitudinal axis 70, the third distance being less than the fourth distance. When stent 82 is in an expanded state, the plurality of troughs 24 of stent 82 are positioned at substantially the same distance from longitudinal axis 70, as shown and described above with respect to FIGS. 3A-3C. FIG. 8B is a cross-sectional view of the example stent and balloon depicted in FIG. 8A, taken along line B-B.

Figure 9:
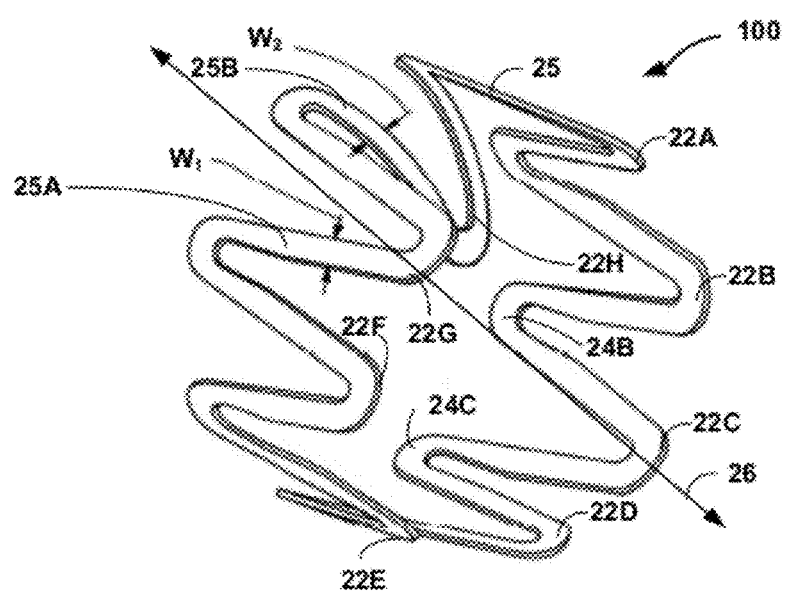
FIG. 9 is an isometric view of another example annular ring of a stent that can be used to implement various techniques of this disclosure.

FIG. 9 is an isometric view of another example annular ring of a stent that can be used to implement various techniques of this disclosure. In FIG. 9, in accordance with this disclosure, bent peak 22H of ring 100 is configured to expand before the unbent peaks, e.g., peaks 22A-22G, when a stent comprising ring 100 transitions from a reduced state to an expanded state. Ring 100 forms part of a stent in a reduced state. FIGS. 3A-3C, described in detail above, depict a ring in an expanded state.

In accordance with certain techniques of this disclosure, bent peak 22H of ring 100 of FIG. 9 is configured to expand before the unbent peaks, e.g., peaks 22A-22G. That is, by constructing struts of the bent peak to be thinner than struts of the unbent peaks, the bent peaks can open prior to the unbent peaks as the stent expands from a reduced state. In FIG. 9, unbent peaks, e.g., unbent peak 22G, is formed by struts 25A having a width $W_1$ and bent peak 22H is formed by struts 25B having a width $W_2$, where width $W_1$ is greater than width $W_2$. Such a configuration allows a bent peak, e.g., peak 22H, that extends into the fold of a balloon, e.g., fold 68 of balloon 64, to expand outwardly prior to the remaining unbent peaks, e.g., 22A-22G, during an expansion from the reduced state to the expanded state. Additional detail regarding stents that include struts with varying widths can be found in U.S. Patent Application No. 61/448,843, entitled "Low Strain High Strength Stent" and filed on Mar. 3, 2011, incorporated herein by reference in its entirety.

It should be noted that although one peak, namely peak 22H, is depicted in FIG. 9 as being bent, two or more peaks can be bent inward, as described in detail above. As such, each bent peak can comprise struts that are thinner than the struts of unbent peaks.

FIG. 10A is an isometric view of another example annular ring of a stent that can be used to implement various techniques of this disclosure. In particular, FIG. 10A depicts annular ring 110 arranged about longitudinal axis 26 and configured to have two peaks that bend inward into a cylindrical volume defined by ring 110 and into a balloon fold of a balloon. In FIG. 10A, peaks 22D and 22H of ring 110 bend inwards into the cylindrical volume defined by the ring. FIGS. 10B and 10C depict a side view and an end view, respectively, of the example annular ring depicted in FIG. 10A.

FIG. 11A is an isometric view of another example annular ring of a stent that can be used to implement various techniques of this disclosure. In particular, FIG. 11A depicts annular ring 110 arranged about longitudinal axis 26 and configured to have four peaks that bend inward into a cylindrical volume defined by ring 110 and into a balloon fold of a balloon. In FIG. 11A, peaks 22B, 22D, 22F, and 22H of ring 110 bend inwards into the cylindrical volume defined by the ring. Ring 110 is similar to ring 50 of FIGS. 5A-5C, except that bent peaks 22B, 22D, 22F, and 22H of ring 110 are deformed even more than the bent peaks of 50. Peaks 22B, 22D, 22F, and 22H of ring 110 can be deformed in the manner shown by adding additional fold lines 29, such as fold lines 29A-29C as seen best in FIG. 11C. FIGS. 11B and 11C depict a side view and an end view, respectively, of the example annular ring depicted in FIG. 11A.

In some examples, the stent, the delivery system or other portion of the assembly may include one or more areas, bands, coatings, members, etc. that is (are) detectable by imaging modalities such as X-Ray, MRI, ultrasound, etc. In other examples, at least a portion of the stent and/or adjacent assembly is at least partially radiopaque.

In some examples, at least a portion of the stent is configured to include one or more mechanisms for the delivery of a therapeutic agent. Often the agent will be in the form of a coating or other layer (or layers) of material placed on a surface region of the stent, which is adapted to be released at the site of the stent's implantation or areas adjacent thereto.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof Where the therapeutic agent includes a polymer agent, the polymer agent may be a polystyrene-polyisobutylene-polystyrene triblock copolymer (SIBS), polyethylene oxide, silicone rubber and/or any other suitable substrate.

The above disclosure is intended to be illustrative and not exhaustive. This description will suggest many variations and alternatives to one of ordinary skill in this art. The various elements shown in the individual figures and described above may be combined or modified for combination as desired. Various examples of the disclosure have been described. These and other examples are within the scope of the following claims.

The invention claimed is:

1. A stent delivery system comprising:
a catheter comprising an expandable balloon, the balloon having a pleated state and an unpleated state, the balloon having at least two pleats in the pleated state, adjacent pleats of a balloon being separated by a fold in the pleated state; and
a stent having a reduced state and an expanded state, the stent comprising a plurality of interconnected annular rings arranged about a longitudinal axis, each of the plurality of annular rings comprising a plurality of peaks and a plurality of troughs,
wherein in the reduced state and positioned on the balloon, at least one of the plurality of peaks of at least one of the plurality of rings extends into a fold of the balloon in the pleated state the at least one peak being positioned a first distance from the longitudinal axis, another one of the plurality of peaks being positioned a second distance from the longitudinal axis, the first distance being less than the second distance,
wherein in the expanded state, the plurality of peaks of the stent being positioned at substantially the same distance from the longitudinal axis,
wherein the plurality of peaks are defined by a plurality of struts,
wherein the at least one peak that extends into the fold comprises at least one first strut having a first thickness,
wherein each of the remaining peaks of the annular band comprise at least one second strut having a second thickness, and
wherein the first thickness is less than the second thickness.

2. The stent delivery system of claim 1,
wherein the at least one peak that extends into the fold comprises at least one first strut having a first width,
wherein each of the remaining peaks of the annular ring comprise at least one second strut having a second width, and
wherein the first width is less than the second width.

3. The stent delivery system of claim 1,
wherein the fold is a first fold of the balloon, and
wherein at least one of the plurality of troughs of at least one of the plurality of rings extends into a second fold of the balloon in the pleated state, the at least one trough being positioned a third distance from the longitudinal axis, another one of the plurality of peaks being positioned a fourth distance from the longitudinal axis, the third distance being less than the fourth distance.

4. The stent delivery system of claim 3,
wherein the plurality of troughs are defined by a plurality of struts,
wherein the at least one trough that extends into the fold comprises at least one first strut having a first thickness,
wherein each of the remaining troughs of the annular ring comprise at least one second strut having a second thickness, and
wherein the first thickness is less than the second thickness.

5. The stent delivery system of claim 1,
wherein in the reduced state and positioned on the balloon, at least one of the plurality of peaks of each of the plurality of rings extends into a fold of the balloon in the pleated state.

6. The stent delivery system of claim 5,
wherein the at least one peak that extends into the fold comprises at least one first strut having a first width,
wherein each of the remaining peaks of the annular ring comprise at least one second strut having a second width, and
wherein the first width is less than the second width.

7. The stent delivery system of claim 1,
wherein during an expansion from the reduced state to the expanded state, the at least one peak that extends into the fold is configured to expand outwardly prior to the remaining peaks.

8. The stent delivery system of claim 7,
wherein the at least one peak configured to expand outwardly prior to the remaining peaks comprises at least one strut having a first width,
wherein the remaining peaks comprise a plurality of struts that each have a second width, and
wherein the first width is less than the second width.

9. A stent having a reduced state and an expanded state, the stent comprising:
a plurality of interconnected annular rings arranged about a longitudinal axis, each of the plurality of annular rings comprising a plurality of peaks and a plurality of troughs,
wherein in the reduced state, at least one of the plurality of peaks of at least one of the plurality of rings is positioned a first distance from the longitudinal axis, another one of the plurality of peaks being positioned a second distance from the longitudinal axis, the first distance being less than the second distance,
wherein in the expanded state, the plurality of peaks of the stent being positioned at substantially the same distance from the longitudinal axis,
wherein the plurality of peaks are defined by a plurality of struts,
wherein the at least one peak positioned a first distance from the longitudinal axis comprises at least one first strut having a first thickness,
wherein each of the remaining peaks of the annular band comprise at least one second strut having a second thickness, and
wherein the first thickness is less than the second thickness.

10. The stent of claim 9,
wherein at least one of the plurality of troughs of at least one of the plurality of rings is positioned a third distance from the longitudinal axis, another one of the plurality of peaks being positioned a fourth distance from the longitudinal axis, the third distance being less than the fourth distance.

11. The stent of claim 10,
wherein the plurality of troughs are defined by a plurality of struts,
wherein the at least one troughs that extends into the fold comprises at least one first strut having a first thickness,
wherein each of the remaining troughs of the annular band comprise at least one second strut having a second thickness, and
wherein the first thickness is less than the second thickness.

12. The stent of claim 10,
wherein the plurality of troughs are defined by a plurality of struts,
wherein the at least one trough positioned a third distance from the longitudinal axis comprises at least one first strut having a first width,
wherein each of the remaining troughs of the annular ring comprise at least one second strut having a second width, and
wherein the first width is less than the second width.

13. The stent of claim 9,
wherein the at least one peak positioned a first distance from the longitudinal axis comprises at least one first strut having a first width,
wherein each of the remaining peaks of the annular ring comprise at least one second strut having a second width, and
wherein the first width is less than the second width.

14. The stent of claim 9,
wherein during an expansion from the reduced state to the expanded state, the at least one peak that is positioned the first distance from the longitudinal axis in the reduced state is configured to expand outwardly prior to the remaining peaks.

15. The stent of claim 14,
wherein the at least one peak configured to expand outwardly prior to the remaining peaks comprises at least one strut having a first width,
wherein the remaining peaks comprise a plurality of struts that each have a second width, and
wherein the first width is less than the second width.

16. A stent having a reduced state and an expanded state, the stent comprising:
a plurality of interconnected annular rings arranged about a longitudinal axis, each of the plurality of annular rings comprising a plurality of peaks and a plurality of troughs,
wherein in the reduced state, at least one of the plurality of peaks of at least one of the plurality of rings is positioned a first distance from the longitudinal axis, another one of the plurality of peaks being positioned a second distance from the longitudinal axis, the first distance being less than the second distance,
wherein in the expanded state, the plurality of peaks of the stent being positioned at substantially the same distance from the longitudinal axis,
wherein the plurality of peaks are defined by a plurality of struts,
wherein the at least one peak positioned a first distance from the longitudinal axis comprises at least one first strut having a first width,
wherein each of the remaining peaks of the annular band comprise at least one second strut having a second width, and
wherein the first width is less than the second width.

17. The stent of claim 16,
wherein at least one of the plurality of troughs of at least one of the plurality of rings is positioned a third distance from the longitudinal axis, another one of the plurality of peaks being positioned a fourth distance from the longitudinal axis, the third distance being less than the fourth distance.

18. The stent of claim 16,
wherein during an expansion from the reduced state to the expanded state, the at least one peak that is positioned the first distance from the longitudinal axis in the reduced state is configured to expand outwardly prior to the remaining peaks.

* * * * *